United States Patent
Barker et al.

(10) Patent No.: US 6,569,115 B1
(45) Date of Patent: May 27, 2003

(54) PRE-FILLED RETRACTABLE NEEDLE INJECTION DEVICE

(75) Inventors: John M. Barker, Ventura, CA (US); Thor R. Halseth, Simi Valley, CA (US); Michael J. Botich, Oxnard, CA (US); Robert L. Hall, Thousand Oaks, CA (US)

(73) Assignee: MDC Investment Holdings, Inc., Wilmington, DE (US)

( * ) Notice: Subject to any disclaimer, the term of this patent is extended or adjusted under 35 U.S.C. 154(b) by 0 days.

(21) Appl. No.: 09/528,634

(22) Filed: Mar. 20, 2000

Related U.S. Application Data (63) Continuation-in-part of application No. 09/139,540, filed on Aug. 26, 1998, now Pat. No. 6,039,713, and a continuation-in-part of application No. PCT/US99/04456, filed on Mar. 1, 1999.

(60) Provisional application No. 60/058,004, filed on Aug. 28, 1997, provisional application No. 60/078,233, filed on Mar. 17, 1998, provisional application No. 60/120,889, filed on Feb. 20, 1999, and provisional application No. 60/152,016, filed on Sep. 1, 1999.

(51) Int. Cl.[7] .............................. A61M 5/00
(52) U.S. Cl. ............... 604/110; 604/195; 604/187; 604/201; 604/203; 604/231
(58) Field of Search .................. 604/110, 195, 604/187, 201, 203, 200, 231–234, 205, 181, 218, 220, 244, 221, 206, 235, 245, 263; 128/919

(56) References Cited

U.S. PATENT DOCUMENTS

| | | |
|---|---|---|
| 4,507,117 A | 3/1985 | Vining |
| 4,666,435 A | 5/1987 | Braginetz |
| 4,747,829 A | 5/1988 | Jacob et al. |
| 4,778,453 A | 10/1988 | Lopez |
| 4,790,827 A | 12/1988 | Haber |
| 4,892,523 A | 1/1990 | Haber |
| 4,900,307 A | 2/1990 | Kulli |
| 4,904,242 A | 2/1990 | Kulli |
| 4,906,236 A | 3/1990 | Alberts |
| 4,915,702 A | 4/1990 | Haber |
| 4,917,673 A | 4/1990 | Coplin |
| 4,947,863 A | 8/1990 | Haber |
| RE33,585 E | 5/1991 | Haber |
| 5,067,490 A | 11/1991 | Haber |
| 5,090,962 A | 2/1992 | Landry |
| 5,098,403 A | 3/1992 | Sampson |
| RE34,045 E | 8/1992 | McFarland |
| 5,169,392 A | 12/1992 | Ranford |
| 5,181,909 A | 1/1993 | McFarlane |
| 5,193,552 A | 3/1993 | Columbus |
| 5,201,708 A | 4/1993 | Martin |
| 5,219,333 A | 6/1993 | Sagstetter |
| 5,232,456 A | 8/1993 | Gonzalez |
| 5,246,428 A | 9/1993 | Falknor |
| 5,267,976 A | 12/1993 | Guerineau |
| 5,290,256 A | 3/1994 | Weatherford |
| 5,308,332 A | 5/1994 | Dillard, III |
| 5,320,606 A | 6/1994 | Jore |
| 5,330,430 A | 7/1994 | Sullivan |
| 5,342,310 A | 8/1994 | Ueyama |

(List continued on next page.)

Primary Examiner—Brian L. Casler
Assistant Examiner—Cris Rodriguez
(74) Attorney, Agent, or Firm—Stephen H. Eland; Dann, Dorfman, Herrell & Skillman (57) ABSTRACT

A needle-bearing device for injecting medicinal fluid from a pre-filled vial is provided. After use, the needle is retracted into the body of the device to prevent inadvertent contact with the sharpened end of the needle. In one embodiment, the invention provides a manually actuable button that effectuates retraction of the needle after use. In another embodiment, retraction is effectuated automatically after the injection is complete.

16 Claims, 10 Drawing Sheets

U.S. PATENT DOCUMENTS

| | | |
|---|---|---|
| 5,360,408 A | 11/1994 | Vailancourt |
| 5,389,085 A | 2/1995 | D'Allessio |
| 5,401,246 A | 3/1995 | Mazur |
| 5,403,287 A | 4/1995 | Talonn |
| 5,417,660 A | 5/1995 | Martin |
| 5,487,732 A | 1/1996 | Jeffrey |
| 5,531,692 A | 7/1996 | Rogers |
| 5,531,706 A | 7/1996 | de la Fuente |
| 5,538,507 A | 7/1996 | De Kler |
| 5,549,572 A | 8/1996 | Byrne |
| 5,573,512 A | 11/1996 | van den Haak |
| 5,601,535 A | 2/1997 | Byrne |
| 5,695,475 A | 12/1997 | Best, Jr. |
| 5,697,908 A | 12/1997 | Imbert et al. |
| 5,709,669 A | 1/1998 | Haining |
| 5,788,677 A * | 8/1998 | Botich et al. ............ 604/195 |
| 5,891,105 A | 4/1999 | Mahurkar |
| 5,957,897 A | 9/1999 | Jeffrey |
| 6,004,296 A | 12/1999 | Jansen et al. |
| 6,099,504 A | 8/2000 | Gross et al. |
| 6,102,893 A | 8/2000 | Aneas |
| 6,123,688 A * | 9/2000 | Botich et al. ............ 604/220 |
| 2001/0008962 A1 | 7/2001 | Forsberg et al. |

* cited by examiner

PRE-FILLED RETRACTABLE NEEDLE INJECTION DEVICE

This application is a continuation-in-part of application Ser. No. 09/139,540, filed Aug. 26, 1998 now U.S. Pat. No. 6,039,713, and a continuation-in-part of PCT/US99/04456, filed Mar. 1, 1999 which claims benefit of U.S. Provisional Application No. 60/058,004 filed Aug. 28, 1997, and U.S. Provisional Application No. 60/078,233 filed Mar. 17, 1998, and U.S. Provisional Application No. 60/120,889 filed Feb. 20, 1999, and U.S. Provisional Application No. 60/152,016 filed Sep. 1, 1999, which are hereby incorporated herein by reference.

FIELD OF THE INVENTION

The present invention relates to pre-filled vials, ampoules, carpules, or cartridges for administering injections of medicinal fluids to patients. More specifically, the invention relates to such devices having a retractable needle feature for rendering the device non-reusable and safely disposable.

BACKGROUND OF THE INVENTION

Various types of medical devices employ a needle for piercing the skin of a patient for diagnostic or therapeutic purposes. One such device is a vial injector. Vial injectors utilize pre-filled vials that have a pre-measured dose of medication. The vial injector is used to inject the medication from the vial into a patient.

Handling of such needle-bearing medical devices after the needle is withdrawn from the patient can result in transmission of various pathogens, most notably human immune virus (HIV), to uninfected medical personnel, due to an inadvertent needle stick. Accordingly, it is desirable to provide a device for injecting medication from a pre-filled vial, wherein the injection needle is retracted into the housing of the device after use.

There are numerous retractable needle medical devices disclosed in the prior art. Typically, to effectuate retraction, the prior art devices require manual actuation by the operator. In many situations, such as an emergency situation, the operator is distracted or rushed so that the manual step necessary to effectuate retraction is not performed, either intentionally or unintentionally. In such instances, the used needle remains exposed, creating a risk of an inadvertent needle stick. Therefore, it would be desirable to provide an automatic needle retraction mechanism in which needle retraction is effectuated by normal operation of the device without the need to perform a separate manual step. It is further desirable to provide a device with a limited number of components so that the device can be produced cost effectively.

SUMMARY OF THE INVENTION

With the foregoing in mind, the present invention provides a medical device for injecting medicinal fluid from a fluid container, such as a vial, into a patient. The device includes a needle that is retracted automatically after use so that the contaminated sharpened tip of the needle is enclosed within the device to prevent inadvertent needle sticks.

The device includes a hollow housing having a generally open rearward end forming a socket. A vial containing a quantity of medicinal fluid is adapted to engage the socket. The needle for injecting the fluid is operable between a projecting position in which the sharpened tip of the needle projects forwardly from the housing and a retracted position wherein the sharpened tip is enclosed within the housing. A biasing element biases the needle toward the retracted position. A needle retainer releasably retains the needle in the projecting position. The needle retainer is operable between a locked position and an unlocked position. In the locked position, the needle retainer releasably retains the needle in the projecting position against the bias of the biasing element. In the unlocked position, the needle is released allowing the biasing element to displace the needle rearwardly. The vial cooperates with the needle retainer so that upon forward displacement of the vial, the vial engages the needle retainer displacing the needle retainer from the locked position to the unlocked position.

DESCRIPTION OF THE DRAWINGS

All of the objects of the present invention are more fully set forth hereinafter with reference to the accompanying drawings, wherein.

DESCRIPTION OF THE PREFERRED EMBODIMENT

Figure 1:
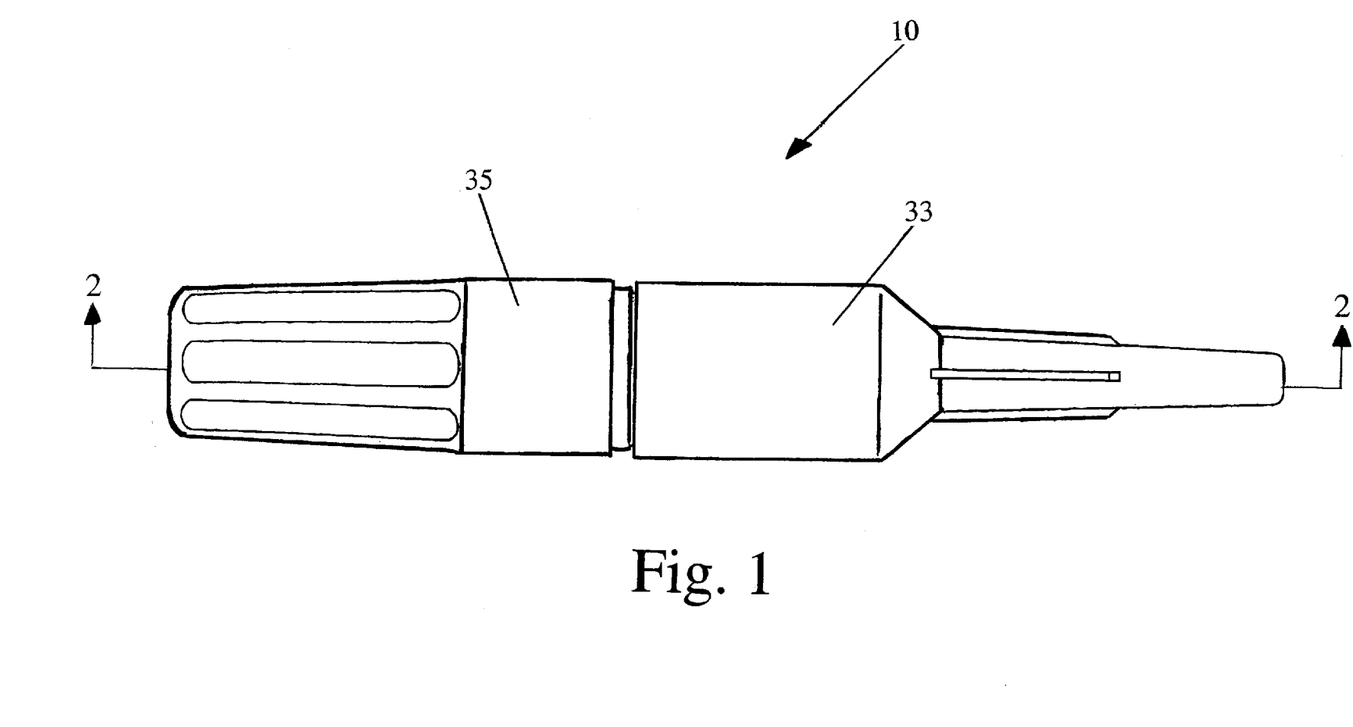
FIG. 1 is a side elevational view of a vial injector having a retractable needle.
Figure 2:
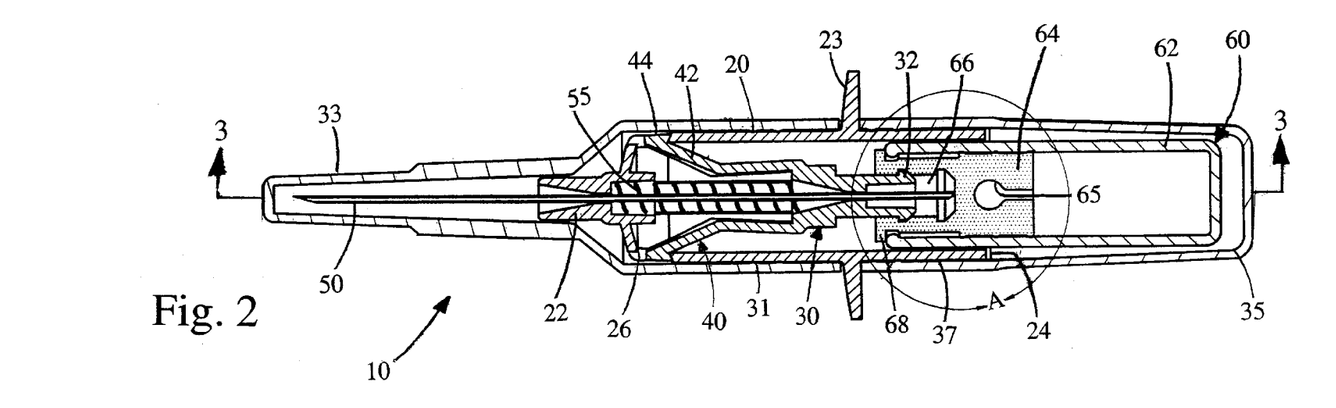
FIG. 2 is a side sectional view of the vial injector shown in FIG. 1, taken along line 2—2.
Figure 3:
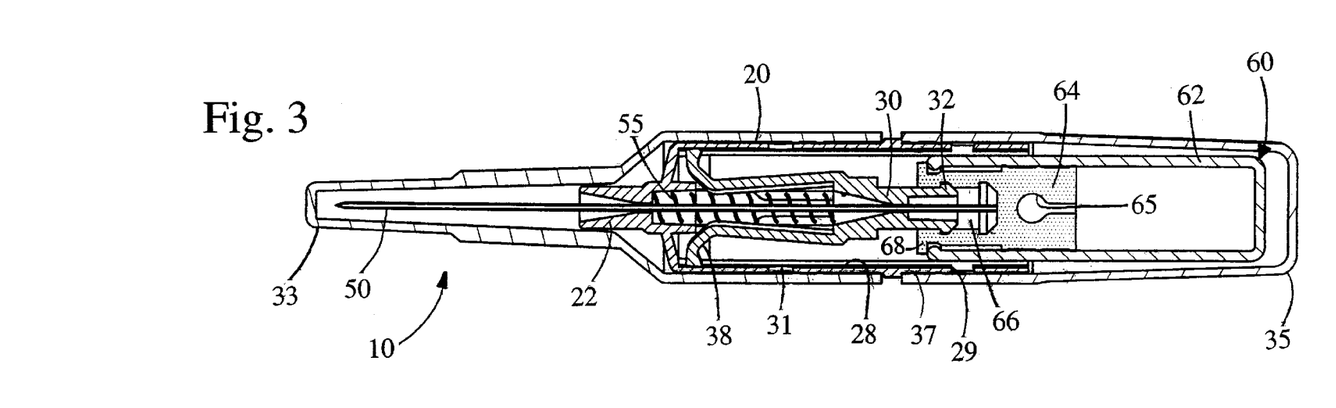
FIG. 3 is a top sectional view of the vial injector shown in FIG. 2, taken along line 3—3.

Referring now to FIGS. 1–12 in general and to FIGS. 1–3 specifically, there is shown a vial injector 10 with an attached vial 60 that is pre-filled with medication. The vial injector 10 includes a needle 50 with a sharpened tip for inserting the needle into a patient. The needle 50 is in fluid communication with the medicine in the vial 60. By pressing the vial 60 into the vial injector 10, the medicine is expelled from the vial and into the patient through the needle 50. After the medicine is administered to the patient, the needle is retracted into body of the vial injector automatically.

Figure 8:
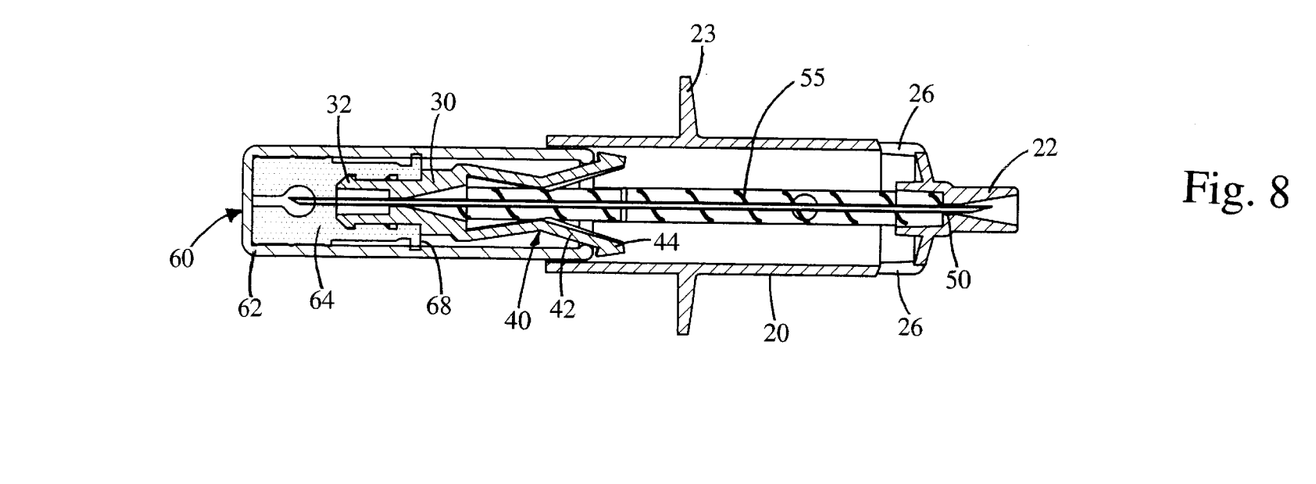
FIG. 8 is a side sectional view of the vial injector shown in FIG. 2, illustrating the needle after retraction.
Figure 9:
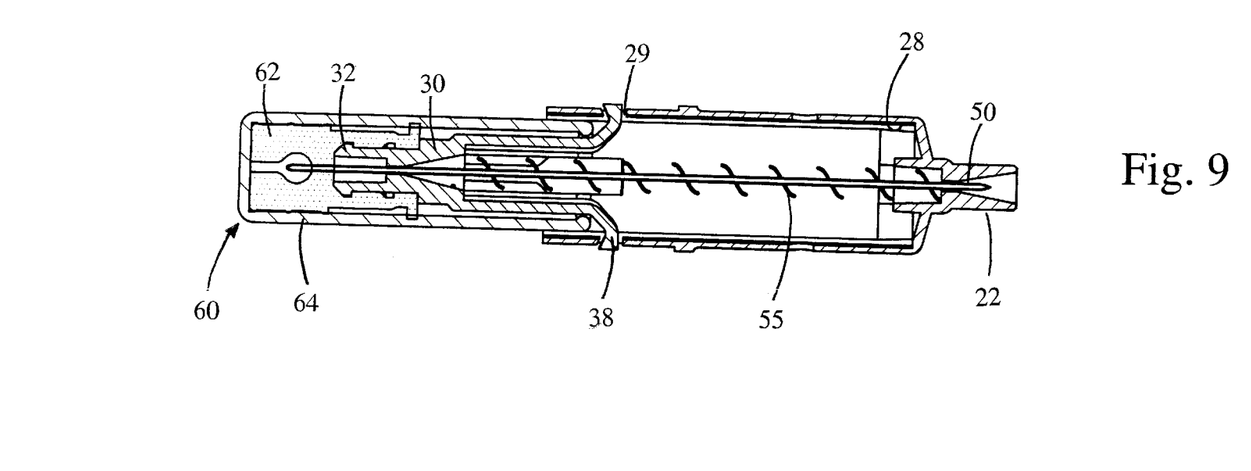
FIG. 9 is a top sectional view of the vial injector shown in FIG. 3, illustrating the needle after retraction.

Referring to FIGS. 1–3, the device 10 includes a generally cylindrical housing 20, a needle 50, a spring 55 biasing the needle rearwardly, and a needle retainer 40 releasably retaining the needle against the bias of the spring. The needle is operable between two positions, a projecting position and a retracted position. In the projecting position, the needle 50 projects forwardly from the forward end of the housing 20. In the retracted position, the needle is retracted into the housing 20 so that the sharpened tip of the needle is enclosed within the housing to prevent inadvertent contact with the sharpened tip. When the needle is in the projecting position, as shown in FIG. 2, the spring biases the needle rearwardly toward the retracted position. The needle retainer 40 releasably retains the needle in the projecting position, against the bias of the spring. The needle retainer cooperates with the vial 60, so that when the vial is displaced forwardly during injection of the medicine, the needle retainer automatically releases the needle and the needle retracts into the housing, as shown in FIGS. 8 and 9.

As shown in FIG. 2, the spring 55 circumscribes the needle 50. A forward end of the spring bears against the interior of the forward portion of the nose 22. The rearward end of the spring bears against the forward end of the plunger 30.

Referring now to FIGS. 2–3, the elements of the device 10 will be described in greater detail. The housing is generally cylindrical and the forward end of the housing has a reduced diameter tapered nose 22. The nose 22 has an opening through which the needle 50 projects outwardly from the housing 20 so that the sharpened tip of the needle can be inserted into a patient for administering medication to the patient. Prior to use, a needle cap encloses the portion of the needle 50 projecting from the housing. The rearward end of the housing 20 is open, forming a cylindrical socket 24 for receiving the vial 60. Two laterally extended flanges 23 project outwardly from the housing 20, transverse the longitudinal axis of the housing, forming two finger grips for operating the device. The housing further includes a pair of locking apertures 26 that cooperate with the needle retainer as described further below.

A plunger 30 is disposed within the housing 20. The needle 50 is fixedly attached to the plunger 30. Specifically, the plunger 30 is a generally cylindrical element having a central bore. The needle is a double ended needle, so that both ends of the needle are sharpened. The needle 50 is disposed within the central bore of the plunger so that the forward portion of the needle projects forwardly from the plunger and the rearward portion of the needle projects rearwardly from the plunger. The needle can be attached to the plunger in one of several ways. For instance, the needle 50 may be attached to the plunger 30 by an adhesive such as a UV curable epoxy. Alternatively, the needle can be molded into the plunger, which is formed of plastic. The rearward end of the plunger 30 forms a stem 32 configured to cooperate with the vial 60, as discussed further below.

The plunger 30 is axially displaceable within the housing 20. Prior to retraction, the plunger is retained in a fixed axial position. The plunger is retained in this fixed position while the medication is being expelled from the vial 60. After use, the plunger and the attached needle are displaced rearwardly.

The needle retainer 40 is operable between a locked position and an unlocked position. In the locked position, the needle retainer 40 releasably retains the plunger 30 and the attached needle 50 in a fixed axial position so that the needle projects forwardly from the housing 20. More specifically, in the locked position the needle retainer engages the housing 20, to retain the plunger 30 and the attached needle against the rearward bias of the spring 55. In the unlocked position, the needle retainer allows the plunger 30 and the needle 50 to be retracted rearwardly. More specifically, in the unlocked position, the needle retainer disengages the housing, so that the spring 55 can propel the needle and the attached plunger rearwardly.

The needle retainer 40 comprises a pair of the elongated resilient arms 42. The arms project forwardly and radially outwardly into engagement with the locking apertures 26 formed in the side of the housing 20. The terminal end of each arm forms a locking tab or detent 44. The locking tabs project into the apertures 26 of the housing 20. Each aperture forms a lip or rim. The locking tabs 44 engage the lip formed by each aperture. In this way, the locking tabs 44 operate as a pair of latches to retain the plunger 30 and the attached needle 50 against the bias of the spring 55.

Referring again to FIGS. 2 and 4, the rearward end of the housing 20 is generally opened, forming a socket for receiving the vial 60. The vial 60 is a generally cylindrical vessel containing an amount of medicinal fluid. In the present instance the vial is formed of a rigid material such as glass. The rearward end of the vial 60 is closed, and the forward end of the vial is sealed by an elastomeric piston or plug 64. The plug 64 is generally cylindrical having a plurality of axially-spaced circumferential ribs frictionally and sealingly engaging the interior of the container to provide a fluid-tight seal, thereby preventing fluid from leaking from the vial. The plug 64 further includes a pierceable septum that is pierceable by the rearward end of the needle 50. The septum reseals around the needle 50 after being pierced, to prevent fluid from leaking from the vial.

Figure 4:
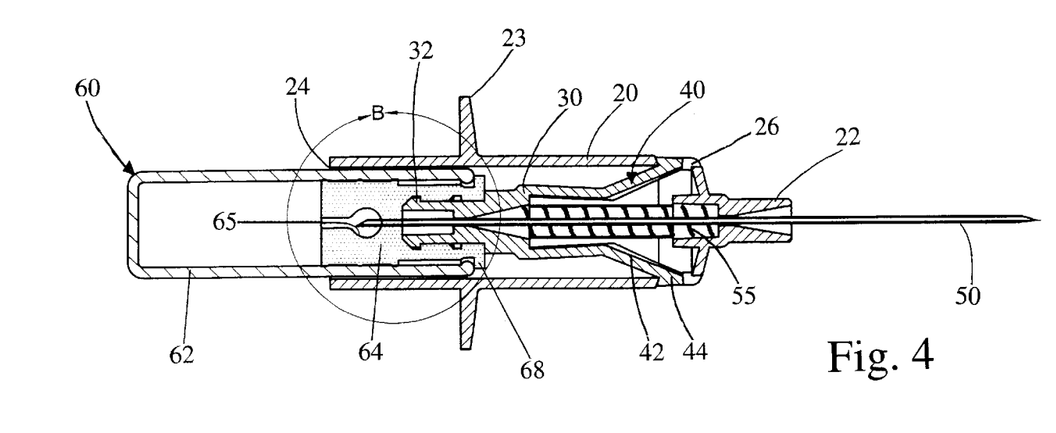
FIG. 4 is a side sectional view of the vial injector shown in FIG. 2, illustrating the device in a "ready for use" position.
Figure 5:
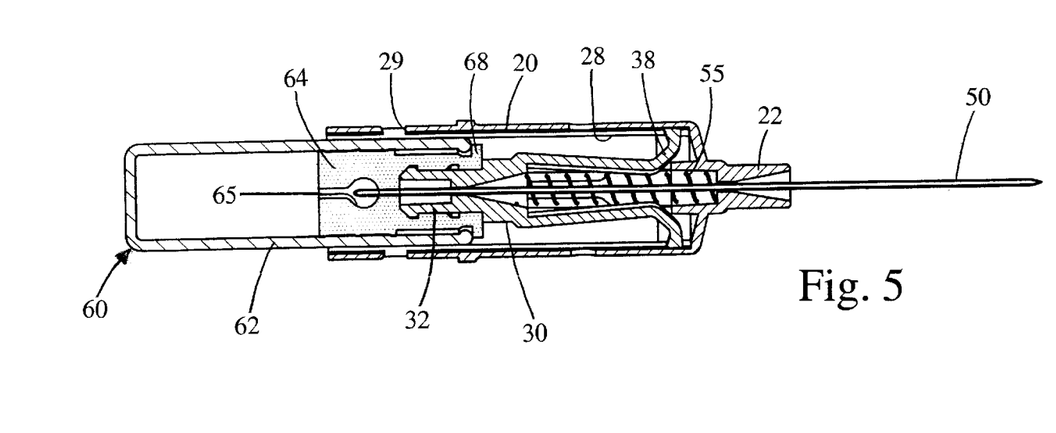
FIG. 5 is a top sectional view of the vial injector shown in FIG. 3, illustrating the device in a "ready for use" position.
Figure 6:
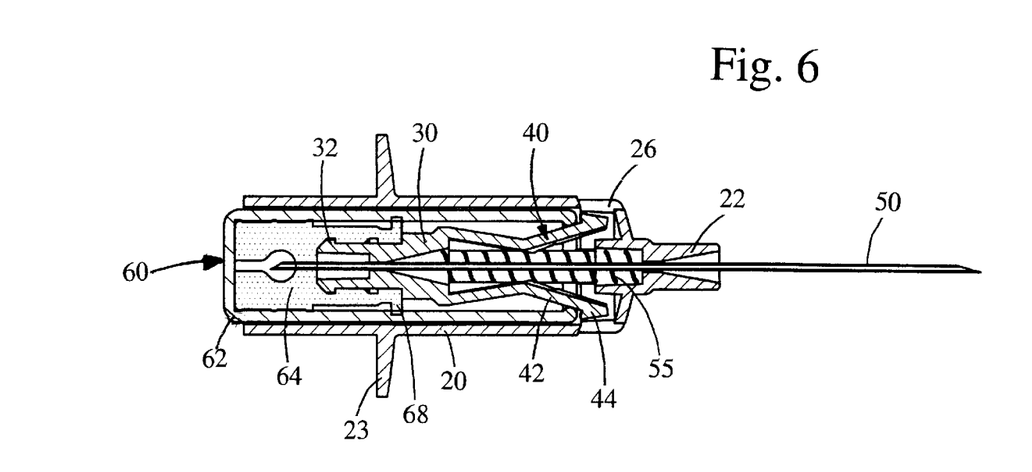
FIG. 6 is a side sectional view of the vial injector shown in FIG. 2, illustrating the needle just prior to retraction.
Figure 7:
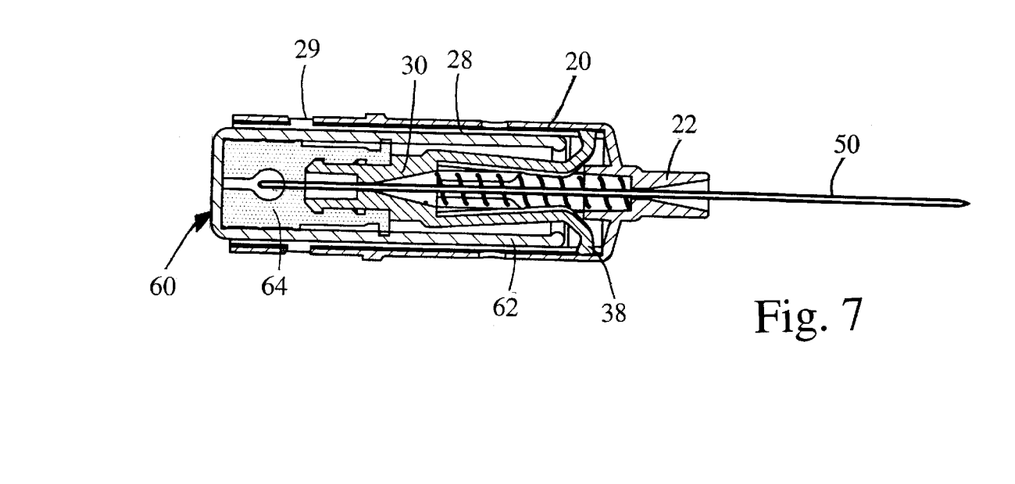
FIG. 7 is a top sectional view of the vial injector shown in FIG. 3, illustrating the needle just prior to retraction.

The plug 64 is configured to cooperate with the mounting stem 32 of the device 10. In the present instance, the mounting stem 32 is a barb and the plug 60 has a corresponding socket 68. The interior end of the plug 64 adjacent the medication includes a recess 65. In this way, a pierceable wall is formed in the plug 64 between the recess 65 and the base of the socket 66. When the vial 60 is mounted on the mounting stem 32, the rearward sharpened end of the needle 50 pierces the wall of the plug and extends into the recess 65 formed in the interior of the plug. The recess 65 opens to the interior of the vial 60 so that when the needle 50 projects into the recess, the needle is in fluid communication with the interior of the vial 60, allowing medication to flow from the vial into the needle. After the needle pierces the wall of the plug, the wall forms a fluid-tight seal between the plug 64 and the side of the needle to prevent medication from leaking into the housing 20.

Figure 10:
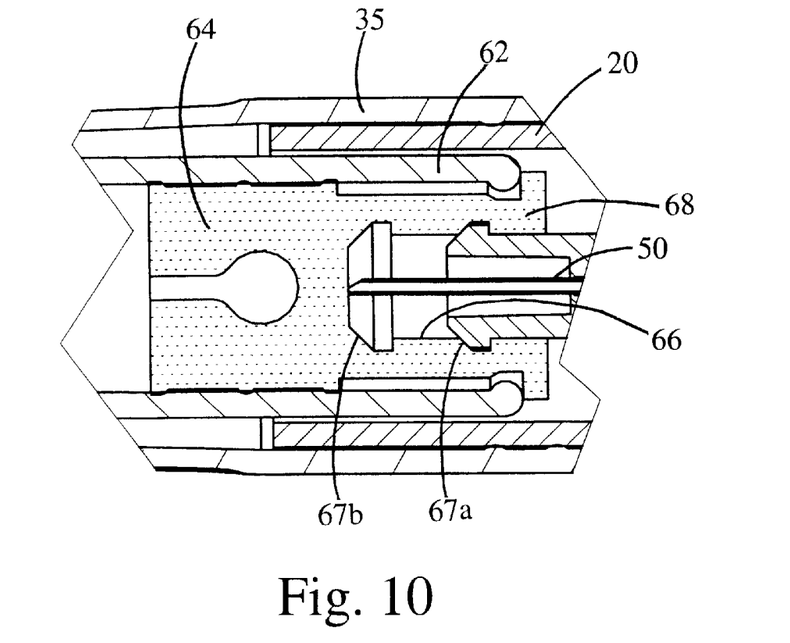
FIG. 10 is an enlarged fragmentary side sectional view of detail A in FIG. 2.
Figure 11:
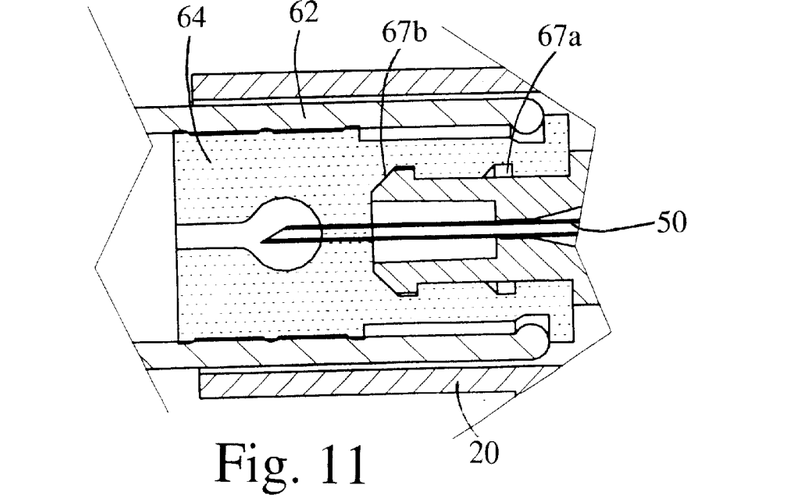
FIG. 11 is an enlarged fragmentary side sectional view of detail B in FIG. 4.

The plug 64 further includes a socket 66 that matingly engages the barb of the mounting stem. Specifically, the socket includes two radially relieved portions or recesses 67a, 67b that mate with the head of the barb. As shown in FIG. 10, prior to use the vial 60 is mounted onto the stem 32 so that the head of the barb engages the first radial recess 67a in the socket. In this position, the needle does not pierce the septum of the piston. To prepare for use, the medical professional displaces the vial forwardly relative to the mounting stem 32, as shown in FIG. 11, thereby displacing the head of the barb into engagement with the second radial recess 67b in the socket 66. At the same time, the needle pierces the septum, so that the needle is in fluid communication with the medicament in the vial.

The connection between the vial 60 and mounting stem 32 is preferably a one-way engagement. In other words, when the vial is mounted on the mounting stem, the vial can be displaced forwardly relative to the mounting stem, but the vial can not be displaced rearwardly relative to the mounting stem. In this way, the vial cannot be readily removed from the mounting stem, such that the vial is substantially permanently attached to the mounting stem.

The one-way connection is provided by the rearward-facing tapered shoulder of the barb 32 and the radial recesses 67a, 67b in the piston, and the sharp or square forward facing shoulders of the barb and the radial recess. The rearward-facing shoulder of the barb and the radial recesses cooperate to permit relative displacement. However, the square shoulders operate as stops impeding relative rearward displacement.

In addition, the plug 64 is configured to prevent ejection of fluid when the vial 60 is displaced from the first position in which the mounting stem 32 engages the first radial recess 67a, to the second position in which the mounting stem engages the second radial recess 67b and the needle 50 pierces the septum. Specifically, the plug 64 includes a flared head 68 or circumferential flange at the forward end. The flared head 68 engages the interior of the container 62 when the vial is displaced from the first position to the second position. The engagement between the flared head and the interior of the container 62 combined with the frictional engagement between the piston and the interior of the container is greater than the force required to displace the piston from the first position to the second position. Accordingly, the container does not move relative to the piston when the vial is displaced into the second position in preparation for an injection. Preventing the container 62 from displacing relative to the piston 64, prevents fluid from being expelled when the needle 50 pierces the septum in the piston.

The medication is expelled from the vial 60 by moving the vial axially forwardly to advance the vial. The plug 64 is mounted on the mounting stem 32 so that the plug remains stationary while the vial 60 is advanced. The plug 64 is configured to form a sliding fit with the interior of the vial so that the vial can slide over the plug to expel the medication from the vial. Additionally, the circumferential ribs maintain a fluid-tight seal between the plug and the vial while the vial slides over the plug.

As the vial 60 is advanced, the medication in the vial flows out of the vial and into the needle. The medication is expelled from the needle into the patient. As described further below, after the medication is injected into the patient, the needle 50 is retracted into the housing 20 so that the forward sharpened tip of the needle is enclosed within the housing 20.

Referring now to FIGS. 4–9, the actuation of the needle retainer 40 is most clearly shown. The forward end of the container 62 forms a rim. As the container 62 is axially advanced, the rim of the container 62 is displaced into engagement with the arms 42 of the needle retainer 40. The container 62 is configured so that the distance between the rearward end of the plug 64 and the rearward end of the vial corresponds to the distance between the rim of the vial and the needle retainer arms 42 when the vial is mounted on the mounting stem 32. In this way, the rim of the container 62 engages the needle retainer arms 42 when substantially all of the medication is expelled from the vial 60.

After the rim of the container 62 engages the needle retainer arms 42, continued axial advancement of the container displaces the arms 42 radially inwardly so that the locking tabs 44 are displaced inwardly, disengaging the locking tabs 44 from the locking apertures 26 of the housing 20. In this way, the vial operates as an actuator such that axial advancement of the vial displaces the needle retainer into the unlocked position. The spring is of sufficient force to overcome the friction between the locking tabs 44 and the interior of the housing 20. After the needle retainer is in the unlocked position and the user releases the vial, the spring 55 propels the needle 50 rearwardly until the forward sharpened tip of the needle is enclosed within the housing 20.

As shown in FIGS. 8 and 9, when the needle 50 is retracted, the needle, the plunger 30, and the vial 60 are displaced rearwardly together. Accordingly, preferably the device 10 includes a mechanism for limiting the rearward travel of the retracted elements. In addition, preferably the device includes an element for limiting the forward displacement of the needle after retraction to prevent the contaminated needle from being re-extended from the housing.

Referring now to FIGS. 3, 5, 7 and 9, the device 10 includes a pair of guide arms 38 that cooperate with a pair of alignment channels or grooves 28 formed in the interior wall of the housing. The guide arms 38 are integrally formed with the plunger 30, and project radially outwardly into engagement with the alignment grooves 28 formed in the housing 20. Each guide arm comprises an axially elongated portion, which preferably is generally parallel to the housing walls. The forward end of each arm turns outwardly transverse the axis of the housing, and into engagement with the alignment groove 28 to constrain the plunger against circumferential displacement relative to the housing. In this way, the plunger is limited to axial displacement.

The axially elongated component of each guide arm 38 is spaced radially inwardly from the inner wall of the housing to create a clearance space. Preferably, the radial thickness of the clearance space is greater than the thickness of the wall of the vial container 62. In this way, when the vial 60 is advanced, the vial does not engage the guide arms 38.

Each alignment groove 28 is substantially parallel to the axis of the housing 20, and terminates prior to the rearward edge of the housing. The rearward portion of each alignment groove 28 intersects a lockout window formed in the wall of the housing. Each guide arm 38 engages the corresponding lockout window at the rearward-most point of retraction, thereby retaining the corresponding guide arm 38 against forward displacement, so that the plunger and the attached needle cannot be displaced forwardly.

Figure 12:
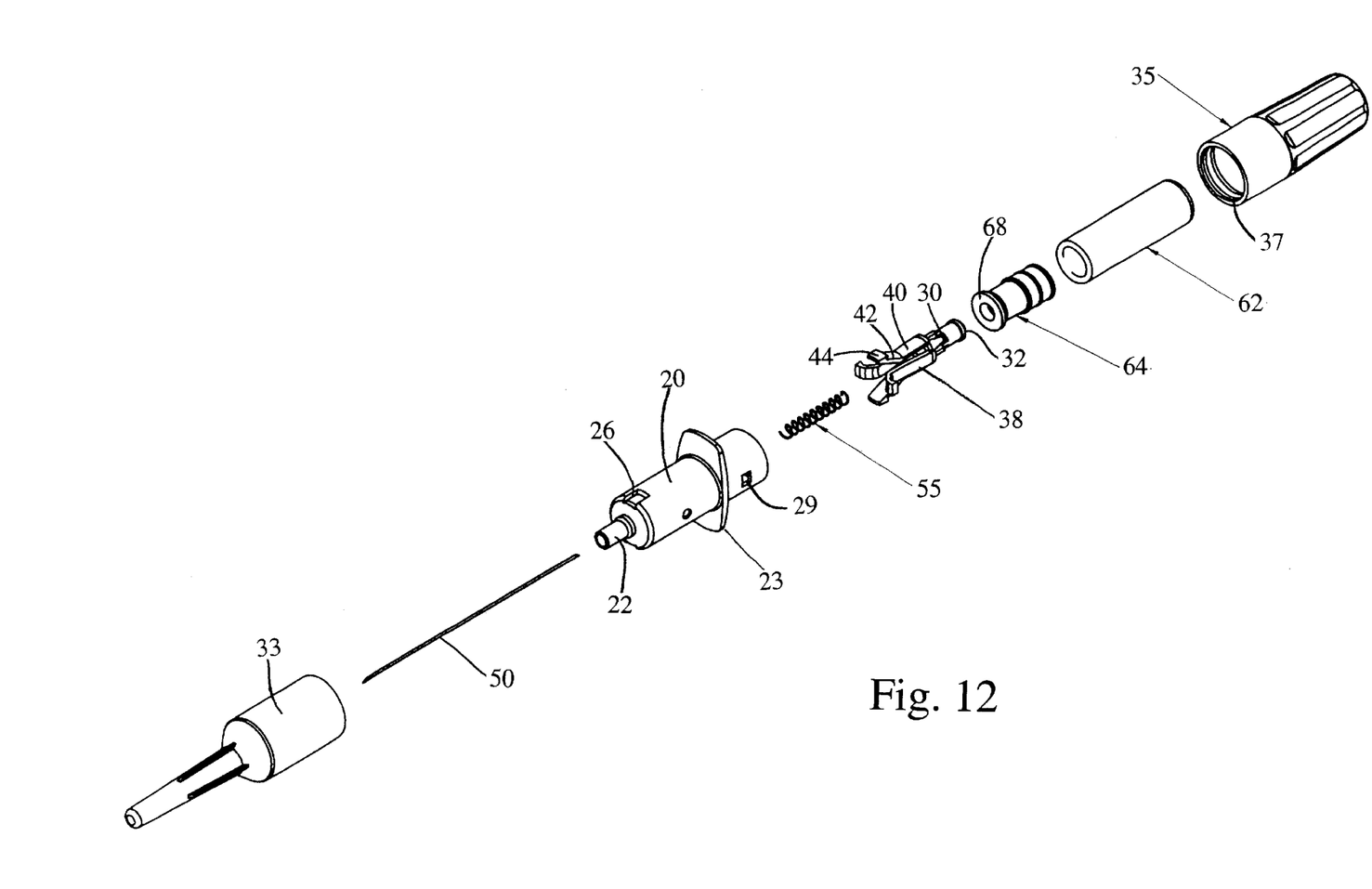
FIG. 12 is an exploded perspective view of the vial injector shown in FIG. 1.

Preferably, the device further includes a front cap 33 and a rear cap 35. The front cap 33 covers the font end of the housing 20 and the front end of the needle 50 prior to use to prevent inadvertent contact with the needle or contamination of the needle. In addition, the front cap 33 operates as a seal to seal the forward end of the housing against entrance of contaminants. Specifically, a plurality of spaced-apart circumferential ribs 31 project from the interior surface of the front cap. The ribs 31 engage the exterior surface of the housing in sealing engagement. In this way, the front cap 33 prevents the migration of contaminant into the housing 20 through either the openings 26 that engage the needle retainer 40, or the forward opening in the nose 22 of the housing 20.

Similarly, the rear cap 35 covers the rearward end of the housing 20 and the vial 60. The rear cap 35 operates as a seal to seal the rearward end of the housing against entrance of contaminants. In addition, the rear cap 35 engages a circumferential flange on the housing 20 that limits the forward displacement of the rear cap. In this way, the rear cap 35 prevents inadvertent displacement of the vial 60, which could cause the piston septum to be inadvertently pierced and inadvertent ejection of the fluid from the vial. Like the front cap 33, the rear cap 35 includes a plurality of spaced-apart circumferential ribs 37 that project radially inwardly from the interior surface of the rear cap. The ribs 37 engage the exterior of the housing in sealing engagement. In this way, the rear cap prevents the migration of contaminants into the housing through the rearward open end of the housing.

Configured as described above, the device 10 operates as follows. The front and rear caps 33, 35 are removed to expose the needle 50 and the vial 60. Prior to use, the needle 50 is disposed in the projecting position so that the sharpened forward tip of the needle projects forwardly from the housing 20. Preferably, the device 10 is shipped with the vial 60 already mounted on the device so that the first recess 67a of the socket 66 on the plug 64 is already engaging the mounting stem 32. Alternatively, the device may be shipped separately from the vial 60 so that the vial must first be attached to the device. The vial 60 is then displaced forwardly relative to the mounting stem 32 so that the mounting stem engages the second recess 67b and the needle pierces the septum of the plug 64.

The needle 50 is then inserted into the patient and the vial 60 is depressed to axially advance the vial, thereby injecting the medicinal fluid from the vial into the patient. At the end of the injection stroke, the vial engages the needle retainer 40, displacing the needle retainer arms 42 radially inwardly thereby actuating the needle retainer to the unlocked position. However, the needle does not retract until the medical professional releases the vial. Once the vial is released, the spring 55 then propels the needle 50 rearwardly so that the contaminated forward sharpened tip of the needle is enclosed within the housing. Accordingly, the medical professional can retain pressure on the vial until after the needle is withdrawn from the patient. The medical professional can then release his or her finger pressure on the vial so that the spring automatically retracts the needle. Alternatively, the medical professional can release his or her finger pressure on the vial after the needle retainer is unlocked and while the needle is still inserted into the patient. The spring 55 then retracts the needle 50, thereby withdrawing the needle from the patient and into the housing.

Figure 13:
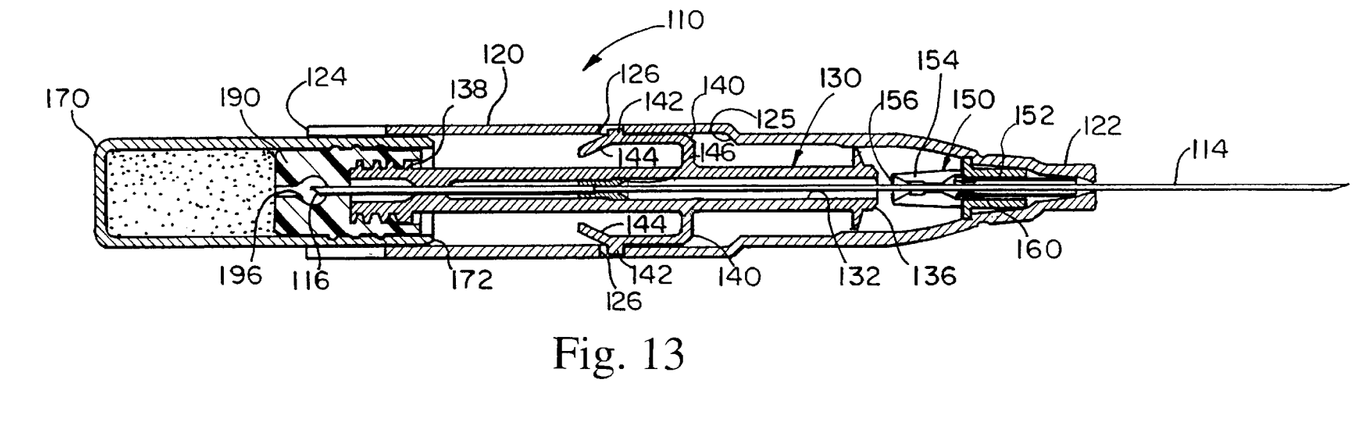
FIG. 13 is a cross-sectional view of an alternate embodiment of a medical device for use in injecting medication from a vial.

Referring now to FIGS. 13–18 in general, and to FIG. 13 specifically, an alternate embodiment of a vial injector 110 is shown. The vial injector 110 includes two needles, an insertion needle 114 and a rearward needle 116 that pierces a plug 190 that seals the vial 170. The insertion needle 114 is operable to inject medication into a patient, and is releasably retained by a needle retainer 150. An actuator 130 cooperates with the needle retainer 150 such that forward axial displacement of the actuator 130 causes the needle retainer 150 to release the insertion needle 114. A spring 160 then propels the insertion needle 114 rearwardly so that the sharpened tip of the needle is located within the vial injector.

The vial injector 110 includes a generally cylindrical hollow barrel 120 having a forward reduced diameter tip 122. The tip 122 is generally closed having a orifice through which the insertion needle 114 projects. The rearward end 124 of the barrel 120 is generally open and is sized to receive the vial 170.

The needle retainer 150 is positioned within the forward end of the barrel 120, adjacent the tip 122. The needle retainer 150 releasably retains the insertion needle 114 so that the insertion needle projects forwardly from the barrel 120 as illustrated in FIG. 13. The needle retainer 150 can be attached to the barrel 120 in a variety of ways, including ultrasonic welding, epoxy, or a snap fit. In the present instance, the needle retainer 150 is attached to the barrel 120 by way of a snap fit.

The insertion needle 114 projects through an axial bore in the needle retainer 150. The needle retainer includes a generally cylindrical body portion 152 at the forward end of the needle retainer and a plurality of axially elongated fingers 154 that releasably retain the insertion needle 114. The fingers 154 have radially inwardly directed protrusions forming a constricted portion in the bore of the needle retainer. Preferably, the surface of each protrusion is configured to conform to the outer surface of insertion needle 114 to maintain the needle in axial alignment with the needle retainer 150. The surfaces of the protrusions preferably form a continuous surface within the interior of the needle retainer to improve engagement with the insertion needle. The fingers 154 are secured or bonded to the outer surface of the insertion needle 114 using an adhesive such as an epoxy. The needle retainer 150 preferably includes four fingers 154, but one or more fingers 154 may be employed depending on such factors as the size of the device and the nature of the biasing member. The exterior of the needle retainer 150 is provided with longitudinal grooves or score lines between the fingers 154 to facilitate separation of the fingers when retraction of the needle is actuated.

Alternatively, the needle retainer 150 can utilize a latching arrangement rather than being releasably bonded to the needle. In the latching arrangement, a block is affixed to the insertion needle 114. The ends of the needle retainer fingers 154 form inwardly directed latches that engage the block to releasably retain the insertion needle.

The needle retainer 150 retains the insertion needle 114 against the rearward bias of a spring 160. In the present instance, the spring 160 is a coil spring that circumscribes the insertion needle 114. As shown in FIG. 13, the forward end of the spring 160 bears against the interior of the barrel tip 122. The rearward end of the spring 160 is attached to the insertion needle 114, preferably by a UV curable adhesive. Alternatively, if the latching arrangement is utilized for the needle retainer 150, then the spring can bear against the block fixed to the needle, if desired.

The vial injector 110 includes an actuator 130 that is operable to engage the needle retainer 150 to cause the needle retainer to release the insertion needle 114 so that the spring 160 propels the insertion needle rearwardly. The actuator 130 is an elongated generally cylindrical member having a hollow axial bore 132. The axial bore 132 has two diameters. The forward portion of the axial bore has a major diameter that is larger than the diameter of the rearward portion of the axial bore. The forward end of the actuator 130 is generally open for receiving the rearward end of the insertion needle 114 that extends into the axial bore 132 of the actuator. A mounting stem 138 is connected to the rearward end of the actuator 130. Preferably, the mounting stem 138 is integrally formed with the actuator 130. In the present instance, the mounting stem 138 includes an externally threaded portion for threadedly engaging a plug 190 in the vial 190. A rearward needle 160 for piercing the plug 190 of the vial 170 projects rearwardly from the mounting stem 138. The rear needle 116 is fixedly connected to the actuator 130, preferably by a UV curable adhesive. The forward portion of the rear needle 114 projects into the axial bore 132 of the actuator 130. Preferably, the rear needle 114 has an internal bore that is larger than the external diameter of the insertion needle 114. In this way, the insertion needle 114 is slidably displaceable within the rear needle 116.

Figure 17:
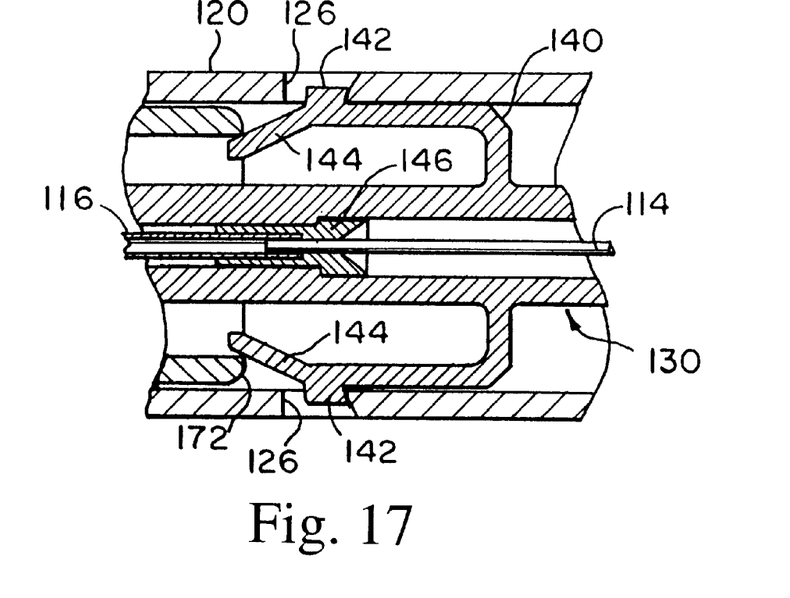
FIG. 17 is an enlarged fragmentary crosssectional view of the device shown in FIG. 14, illustrating details of the safety latch in a latched position.
Figure 18:
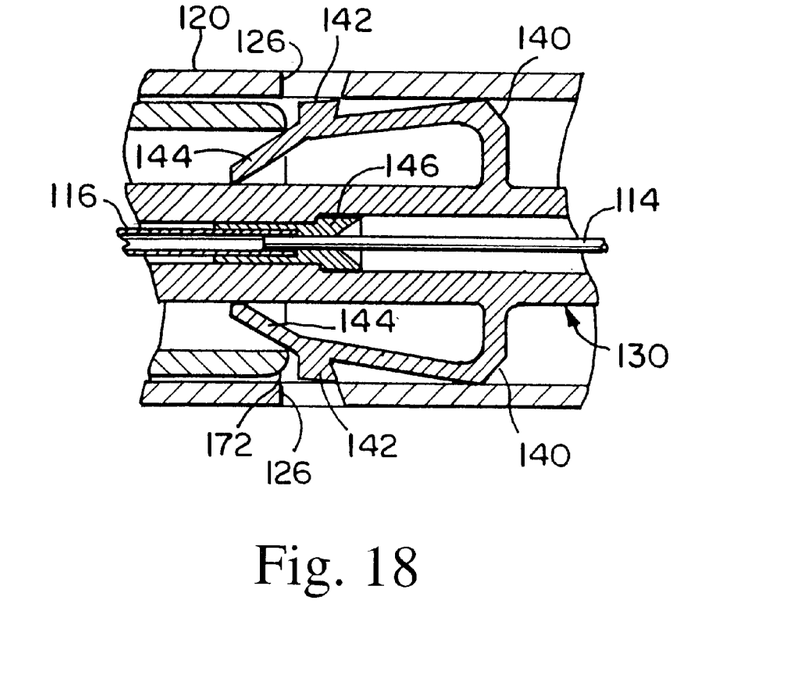
FIG. 18 is an enlarged fragmentary view of the device shown in FIG. 15, illustrating details of the safety latch in an unlatched position.

As shown most clearly in FIG. 17, a seal 146 provides a fluid tight seal between the insertion needle 114 and the rear needle 116. The rear portion of the seal 146 includes a bore sized to receive the forward end of the rear needle 116. The forward portion of the seal 146 includes a constricted portion sized to receive the smaller diameter insertion needle 114, providing a fluid tight seal around the external surface of the insertion needle.

Figure 14:
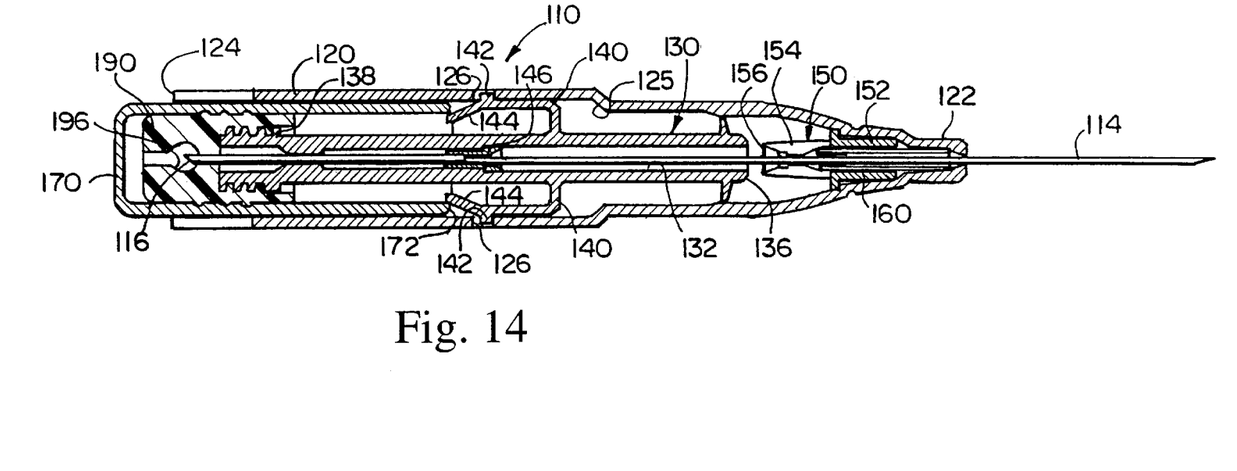
FIG. 14 is a cross-sectional view of the device shown in FIG. 13, illustrating the device in a position just prior to release of a safety latch.
Figure 15:
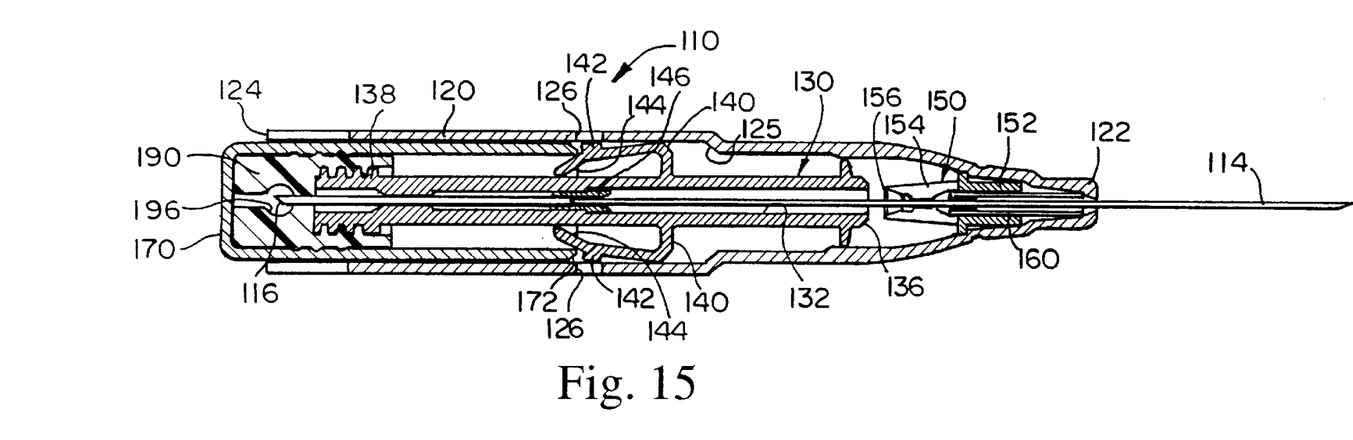
FIG. 15 is a cross-sectional view of the device shown in FIG. 13, illustrating the device in a position just subsequent to release of the safety latch.

The forward end 136 of the actuator 130 is configured to cooperate the rearward end of the fingers 154 of the needle retainer 150. In the present instance, the forward end 136 of the actuator forms a tapered or frustoconical surface. The rearward end of each needle retainer finger 154 tapers radially inwardly so that the rearward end of the needle retainer 150 forms a convergingly tapered annular surface 156. Configured in this way, as shown in FIGS. 14 and 15, when the actuator 130 is axially displaced forwardly to engage the needle retainer 150, the cooperating tapered surfaces of the actuator and the needle retainer operate as a wedge to displace the needle retainer fingers 154 radially outwardly so that the needle retainer releases the insertion needle 114. The spring 160 then propels the insertion needle 114 rearwardly so that the sharpened point of the insertion needle is located within the housing beyond the reach of the operator.

The vial injector 110 preferably includes at least one, and preferably two, safety latches 140 that prevent the actuator 130 from being displaced forwardly until some, and preferably substantially all, of the medication is expelled from the vial 170. Each safety latch 140 is attached to the actuator 130, and in the present instance, the safety latches are integrally formed with the actuator. Each safety latch 140 is a flexible generally L-shaped arm. The forward end of the to safety latch 140 is attached to the actuator 130 and the safety latch extends rearwardly. Each safety-latch includes a detent 142 that cooperates with an aperture 126 formed in the wall of the barrel 120. In this way, as shown in FIG. 14, when the detent 142 of the safety latch 140 projects into the aperture 126, the safety latch 140 prevents the actuator 130 from being displaced axially forwardly.

Referring now to FIG. 17, preferably, the forward end of the detent 142 and the forward end of the aperture 126 are matingly tapered to improve the locking engagement of the detent with the aperture. The portion of the safety latch rearward of the detent 142 projects radially inwardly toward the actuator 130, forming a release tab 144. The forward end or rim 172 of the vial 170 cooperates with the release tab 144 to release the safety latch 140 as will be discussed further below.

Referring again to FIG. 13, the rearward end of the barrel 120 is generally opened, forming a socket 124 for receiving the vial 170. The vial 170 is a generally cylindrical vessel containing an amount of medicinal fluid. The rearward end of the vial 170 is closed, and the forward end of the vial is open forming a rim 172. The open end of the vial 170 is sealed by a rubber piston or plug 190. The plug 190 is generally cylindrical having a plurality of axially-spaced circumferential ribs 192 that form a fluid-tight seal between the plug 190 and the internal surface of the vial 170.

The forward or external end of the plug is configured to cooperate with the mounting stem 138 of the vial injector. In the present instance, the mounting stem 138 is externally threaded and the plug 190 has corresponding internal threads. The interior end of the plug 190 adjacent the medication includes a recess 196. In this way, a pierceable wall is formed in the plug 190 between the recess 196 and the base of the internal threads. When the vial 170 is mounted on the mounting stem 138, the rear needle 116 pierces the wall of the plug and extends into the recess 196 formed in the interior of the plug. The recess opens to the interior of the vial 170 so that when the rear needle 116 projects into the recess 196, the rear needle is in fluid communication with the interior of the vial 170, allowing medication to flow from the vial into the rear needle. After the rear needle 116 pierces the wall of the plug, the wall forms a fluid-tight seal between the plug 190 and the side of the rear needle to prevent medication from leaking into the barrel 120.

The medication is expelled from the vial 170 by moving the vial axially forwardly to advance the vial. The plug 190 is mounted on the mounting stem 138 so that the plug remains stationary while the vial 170 is advanced. The plug 190 is configured to form a sliding fit with the interior of the vial so that the vial 170 can slide over the plug to expel the medication from the vial. Additionally, the circumferential ribs 192 maintain a fluid-tight seal between the plug and the vial while the vial slides over the plug.

As the vial 170 is advanced, the medication in the vial flows out of the vial and into the rear needle 116. From the rear needle 116, the medication flows into the insertion needle 114 and then into the patient. After the medication is injected into the patient, the insertion needle 114 can be retracted into the housing 120 as follows.

Figure 16:
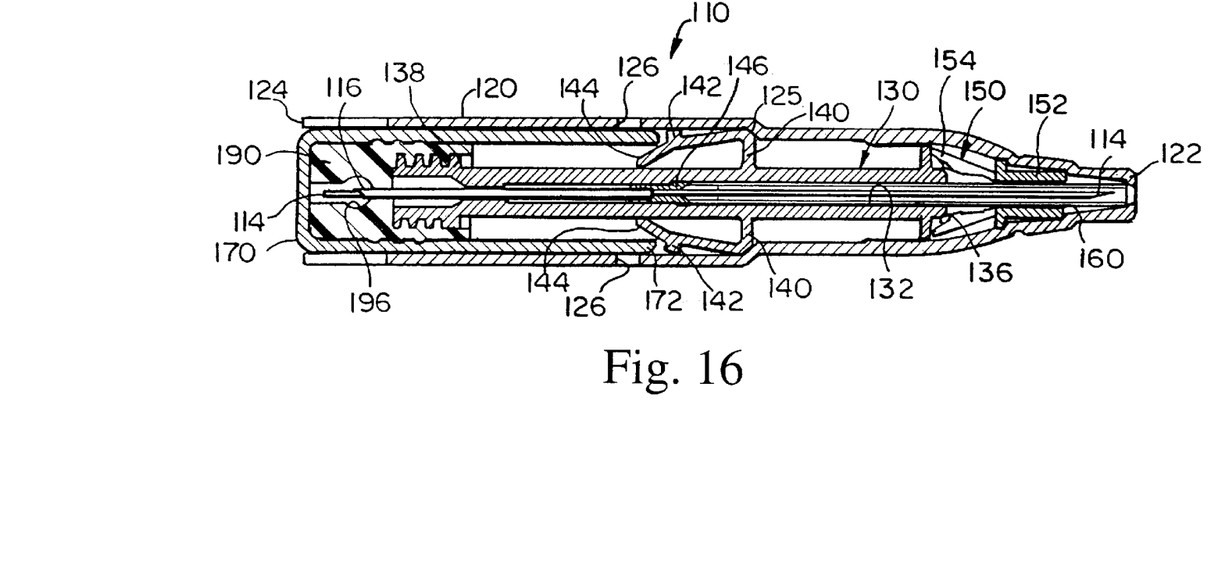
FIG. 16 is a cross-sectional view of the device shown in FIG. 13, illustrating the insertion needle in a retracted position

Referring now to FIGS. 14–16, when at least substantially all of the medication is expelled from the vial 170, the forward rim 172 of the vial engages the release tab 144 of each safety latch 140. Continued forward displacement of the vial 170 flexes each safety latch 140, displacing the safety latches radially inwardly thereby withdrawing the detents 142 from the apertures 126 in the barrel 120. After the detents 142 are withdrawn from the apertures 126, continued forward displacement of the vial 170 displaces the actuator 130 axially forwardly. The actuator 130 then engages the needle retainer 150 to release the insertion needle 114 as shown in FIG. 17 and described previously. In this way, the safety latches 140 prevent the forward axial displacement of the actuator 130 preferably until at least substantially all of the medication is expelled from the vial 170. After at least substantially all of the medication has been expelled from the vial 170, the safety latch 140 releases the actuator allowing the actuator 130 to engage the needle retainer 150 to release the insertion needle 114.

As shown in FIG. 16, the spring 160 propels the insertion needle 114 rearwardly so that the insertion needle telescopes within the rear needle 116. In addition, as shown in FIG. 16, preferably the barrel 120 includes a reduced diameter forward portion forming an internal annular shoulder 125 that engages the forward portion of the safety latches 140. In this way, the internal shoulder 125 acts as a stop to prevent further forward axial displacement of the actuator. The terms and expressions which have been employed are used as terms of description and not of limitation. There is no intention in the use of such terms and expressions of excluding any equivalents of the features shown and described or portions thereof. It is recognized, however, that various modifications are possible within the scope and spirit of the invention. For instance, the second embodiment described above can include a manually actuable release for releasing the safety latches 140 so that the actuator can be actuated to effectuate retraction before substantially all of the medication is expelled from the vial. Accordingly, the invention incorporates variations that fall within the scope of the following claims.

That which is claim is:

1. A medical device operable in connection with a fluid container, comprising:
   a housing having an opening for receiving the fluid container;
   a needle having a sharpened tip movable between a projecting position in which the sharpened tip project forwardly from the housing and a retracted position in which the sharpened tip of the needle is within the housing;
   a biasing element biasing the needle toward the retracted position; and
   a needle retainer comprising a latch biased radially outwardly, releasably engaging the housing wherein the needle retainer is operable between a first position in which the needle retainer releasably retains the needle in the projecting position against the bias of the biasing element and a second position for permitting movement of the needle into the retracted position; wherein displacement of the fluid container toward the needle retainer operates to displace the needle retainer into the second position for permitting retraction of the sharpened tip to the retracted position.

2. The medical device of claim 1 wherein the needle retainer comprises a tapered actuation surface wherein engaging the actuation surface operates to radially displace the needle retainer.

3. The medical device of claim 1 wherein the fluid container has a generally closed rearward end having a fixed rearward wall, a generally open forward end, and a seal sealing the forward end of the fluid container and the device comprises a piercing element operable to pierce the seal permitting fluid to flow between the fluid container and the needle.

4. The medical device of claim 3 wherein the device maintains the seal in a fixed axial position while fluid flows between the fluid container and the needle during use.

5. The medical device of claim 1 wherein the needle retainer comprises at least one axially elongated radially deformable finger.

6. The medical device of claim 5, wherein the needle retainer comprises a plurality of axially elongated fingers and the biasing element is disposed about the needle between the needle and the fingers.

7. The device of claim 1 comprising a seal sealing the fluid container and a mounting stem adapted to engage the seal, wherein the seal and mounting stem are retained against axial displacement while fluid is expelled from the fluid container.

8. The device of claim 7 wherein rearward displacement of the needle displaces the seal and mounting stem.

9. A method for establishing fluid communication between a patient and a fluid container for therapeutic or diagnostic purposes, comprising the steps of:
   providing a fluid container having a pierceable seal;
   providing a medical device having a housing, a needle projecting forwardly from the housing that is biased into the housing, a stem connectable with the seal of the fluid container, and a releasable connection between the needle and the housing, releasably retaining the needle against the bias;
   inserting the fluid container into the housing;
   piercing the seal to provide fluid communication between the fluid container and the needle;
   inserting the needle into the patient to transmit fluid between the patient and the fluid container;
   axially advancing the fluid container so that the fluid container engages the connection between the housing and the needle to automatically retract the needle, stem and seal into the housing.

10. The method of claim 9 wherein the connection between the housing and the needle comprises a needle retainer having an axially elongated radially deformable finger, and axial advancement of the fluid container operates to radially deform the finger to actuate retraction.

11. The method of claim 9 comprising the step of maintaining the seal in an axially fixed position while fluid is transmitted between the patient and the fluid container.

12. A medical device, comprising:
   a fluid container, comprising:
      a seal sealing the fluid container;
      a mounting stem adapted to engage the seal, wherein the seal and mounting stem are retained against axial displacement while fluid is expelled from the fluid container;
   a housing having an opening for receiving the fluid container;
   a needle having a sharpened tip movable between a projecting position in which the sharpened tip project forwardly from the housing and a retracted position in which the sharpened tip of the needle is within the housing;
   a biasing element biasing the needle toward the retracted position;
   a needle retainer operable between a first position in which the needle retainer releasably retains the needle in the projecting position against the bias of the biasing element and a second position for permitting movement of the needle into the retracted position; wherein displacement of the fluid container toward the needle retainer operates to displace the needle retainer into the second position for permitting retraction of the sharpened tip to the retracted position;
   wherein rearward displacement of the needle displaces the seal and mounting stem.

13. The medical device of claim 12 wherein the needle retainer comprises a tapered actuation surface wherein engaging the actuation surface operates to radially displace the needle retainer.

14. The medical device of claim 12 wherein the device maintains the seal in a fixed axial position while fluid flows between the fluid container and the needle during use.

15. The medical device of claim 12, wherein the needle retainer comprises a plurality of axially elongated radially deformable fingers and the biasing element is disposed about the needle between the needle and the fingers.

16. The medical device of claim 12, wherein the needle retainer comprises a latch biased radially outwardly, releasably engaging the housing.

* * * * *